United States Patent [19]

Crawford et al.

[11] 4,380,239

[45] Apr. 19, 1983

[54] INTUBATION OF LACRIMAL DUCTS

[75] Inventors: John S. Crawford; Roy Wainman, both of Toronto, Canada

[73] Assignee: The Hospital For Sick Children, Toronto, Canada

[21] Appl. No.: 309,527

[22] Filed: Oct. 7, 1981

Related U.S. Application Data

[63] Continuation of Ser. No. 104,793, Dec. 20, 1979, abandoned.

[51] Int. Cl.³ ............................................. A61M 27/00
[52] U.S. Cl. ....................................... 604/28; 604/175
[58] Field of Search ............................ 128/348–350 R, 128/341

[56] References Cited

U.S. PATENT DOCUMENTS

| | | | |
|---|---|---|---|
| 2,154,968 | 4/1939 | Alkio | 128/348 |
| 2,221,138 | 11/1940 | Hendrikson | 128/341 |
| 3,726,284 | 4/1973 | Parker | 128/350 R |
| 3,948,272 | 4/1976 | Guibor | 128/350 R |
| 4,305,395 | 12/1981 | Martinez | 128/348 |

FOREIGN PATENT DOCUMENTS 781760  3/1935  France ............................... 128/341

OTHER PUBLICATIONS

Quickert et al., "Probes for Intubation in Lacrimal Drainage", Trans. Amer. Acad. Ophth. & Otol., vol. 74, Mar.–Apr. 1970, pp. 431–433.

*Primary Examiner*—Dalton L. Truluck
*Attorney, Agent, or Firm*—Hirons, Rogers & Scott

[57] ABSTRACT

The invention provides a probe set for use particularly in the canaliculus intubation of the lacrimal duct, the probe set comprising: a probe of a light wire which can be readily deflected through an angle of at least 90 degrees to permit the probe to pass from the nasolacrimal duct to the inferior meatus, the probe having an enlarged end portion which is rounded to limit the possibility of damage to tissue when the probe is inserted; and a very flexible tube of minimal rigidity having a first end attached to an end of the probe remote from the end portion and having an outside diameter comparable to that of the end portion so that in use the probe can be inserted and used to draw the tube into the lacrimal duct.

8 Claims, 4 Drawing Figures

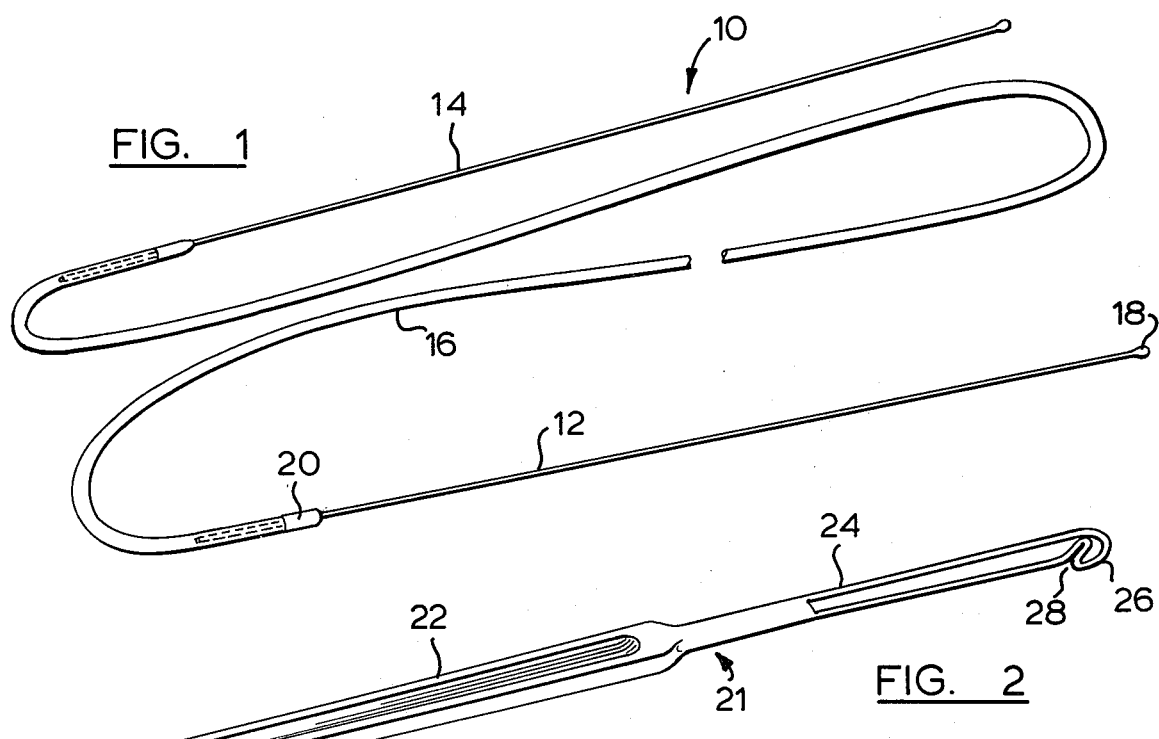
FIG. 1
FIG. 2
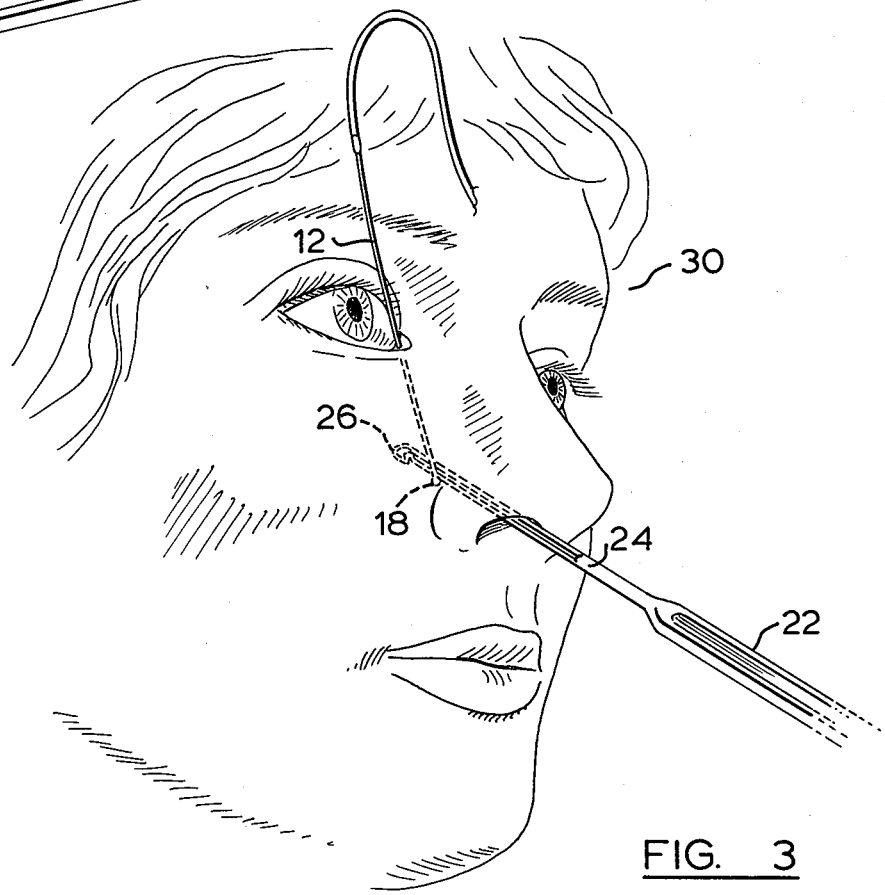
FIG. 3

INTUBATION OF LACRIMAL DUCTS

This application is a continuation of Ser. No. 104,793, filed 12-20-79, now abandoned.

This invention relates to apparatus for intubation of the lacrimal ducts.

Lacrimal fluid (commonly called "tears") is normally supplied continuously to the eye socket from the lacrimal gland. Under normal conditions, excess fluid may be drained through canaliculi or small passageways commencing adjacent the inner corner of the eye. The fluid is collected in the lacrimal sac and then drained via the nasolacrimal duct which leads the fluid to the inferior nasal meatus. For the purposes of this disclosure, the passages forming the drainage system will be referred to collectively as the lacrimal ducts.

In the event that the lacrimal ducts become blocked, the fluid can no longer flow to the nasal meatus. Such closure can result from congenital anomalies, accidents, inflammation and advanced aging, as well as other physiological conditions. The result is that the eye is continually brimming over with fluid causing much personal discomfort to the patient.

One approach to correcting a blocked lacrimal duct is described in U.S. Pat. No. 2,154,968 to Alkio which issued in 1939. This patent teaches a structure consisting of several parts including a rigid tubular probe which contains a very flexible, fine wire. The end of the wire is enlarged to retain the wire in the tube and the probe is inserted through the lacrimal duct until it projects into the inferior meatus of the nose. Then, by withdrawing the tube partially, the wire can be withdrawn through the meatus using a tool which traps the enlarged end of the wire. The flexibility of the wire permits the wire to bend with minimal resistance where the nasolacrimal duct meets the inferior meatus. A spiral canula is then slipped up the wire and into the lacrimal duct so that the wire can then be withdrawn upwardly leaving the spiral canula in place.

With the advent of synthetic plastic materials, and in particular the availability of silicone rubber, attempts were made to insert silicone rubber tubing into the lacrimal duct. The most successful attempt appears to be that of Doctor Pierre Guibor who presented his Canaliculus Intubation Set as a new instrument at the 79th annual meeting of the American Academy of Ophthalmology and Otolaryngolgy which was held in Dallas, Tex. on Oct. 6th to 10th of 1974. In his paper, Dr. Guibor described a structure consisting of a pair of quite stiff stainless steel probes attached one to each end of a length of Silastic tubing (Dow Corning). The tubing has a length of about 29 cm, an inside diameter of 0.063 cm and an outside diameter of 0.119 cm. The tubing is bonded to end portions of the probes which are of tempered stainless steel having a diameter of 0.05 cm and a pre-formed contoured running arch of a length of 17.7 cm. The probes have sufficient stiffness to ensure that the running arch tends to maintain its shape in use. In this respect, the Guibor structure has a similarity to the Alkio structure because in both structures the probe is quite stiff and is designed to retain its shape as it is pushed downwardly into the lacrimal duct. This stiffness was apparently considered to be necessary in such devices. This is in marked contrast with the present invention as will become apparent.

In Dr. Guibor's intubation technique, the probe is passed downwardly through the canaliculus via the common canaliculus and into the lacrimal sac where it is arched superiorly and directed through the nasal lacrimal duct into the inferior meatus of the nose. At this point, the end of the probe must be found using a sterile lighted nasal speculum. A curved Kelly clamp is then used to grasp the tip of the probe and to apply sufficient force to deflect the probe and to pull the probe out of the nose.

U.S. Pat. No. 3,948,272 issued on Apr. 6th, 1976 in the name of Pierre Guibor with Procedure Medical Products Inc. as assignee. This patent shows a structure such as that described in Dr. Guibor's paper although the method of use is described differently and one of the drawings (FIG. 3) does not appear to illustrate the invention. According to the patent, the physician grasps only the tip of the probe as it enters one nostril of the nose and then gently directs it upwards into the lacrimal duct. Subsequently, the probe, having been guided in an arc, is grasped upon exit from the inner corner of the eye by a Kelly clamp.

Although the structure taught by Guibor is probably the most successful to date, it has some marked disadvantages. Firstly, although the quite stiff curved probe has advantages for insertion through the lacrimal duct, the stiffness makes it difficult to withdraw the end of the probe from the interior meatus without damaging the surrounding tissue. Secondly, it is most difficult to find the end of the probe and to apply a Kelly clamp to withdraw the probe. It has been found that it is not uncommon for the procedure to take as much as one and one half hours and for the patient to experience some discomfort as a result of the exploration necessary to find the end of the probe.

Accordingly, it is an object of the present invention to provide apparatus for canaliculus intubation which avoids the disadvantages of the prior art and which limits the possibility of damage to the tissue surrounding the lacrimal duct and inferior meatus.

It is a further object of the invention to provide apparatus for canaliculus intubation which avoids the need for Kelly clamps and makes the insertion of a tube in the lacrimal duct a relatively simple and straight-forward procedure.

The invention provides a probe set for use particularly in the canaliculus intubation of the lacrimal duct, the probe set comprising: a probe of a light wire which can be readily deflected through an angle of at least 90 degrees to permit the probe to pass from the nasolacrimal duct to the inferior meatus, the probe having an enlarged end portion which is rounded to limit the possibility of damage to tissue when the probe is inserted; and a very flexible tube of minimal rigidity having a first end attached to an end of the probe remote from the end portion and having an outside diameter comparable to that of the end portion so that in use the probe can be inserted and used to draw the tube into the lacrimal duct.

The invention will be better understood with reference to the following description taken in combination with the drawings in which:

FIG. 1 is a perspective view of a preferred embodiment of a probe set;

FIG. 2 is a perspective view of a preferred embodiment of a tool for use with the probe set; and FIGS. 3 and 4 illustrate the use of the probe set and tool on a patient.

Figure 4:
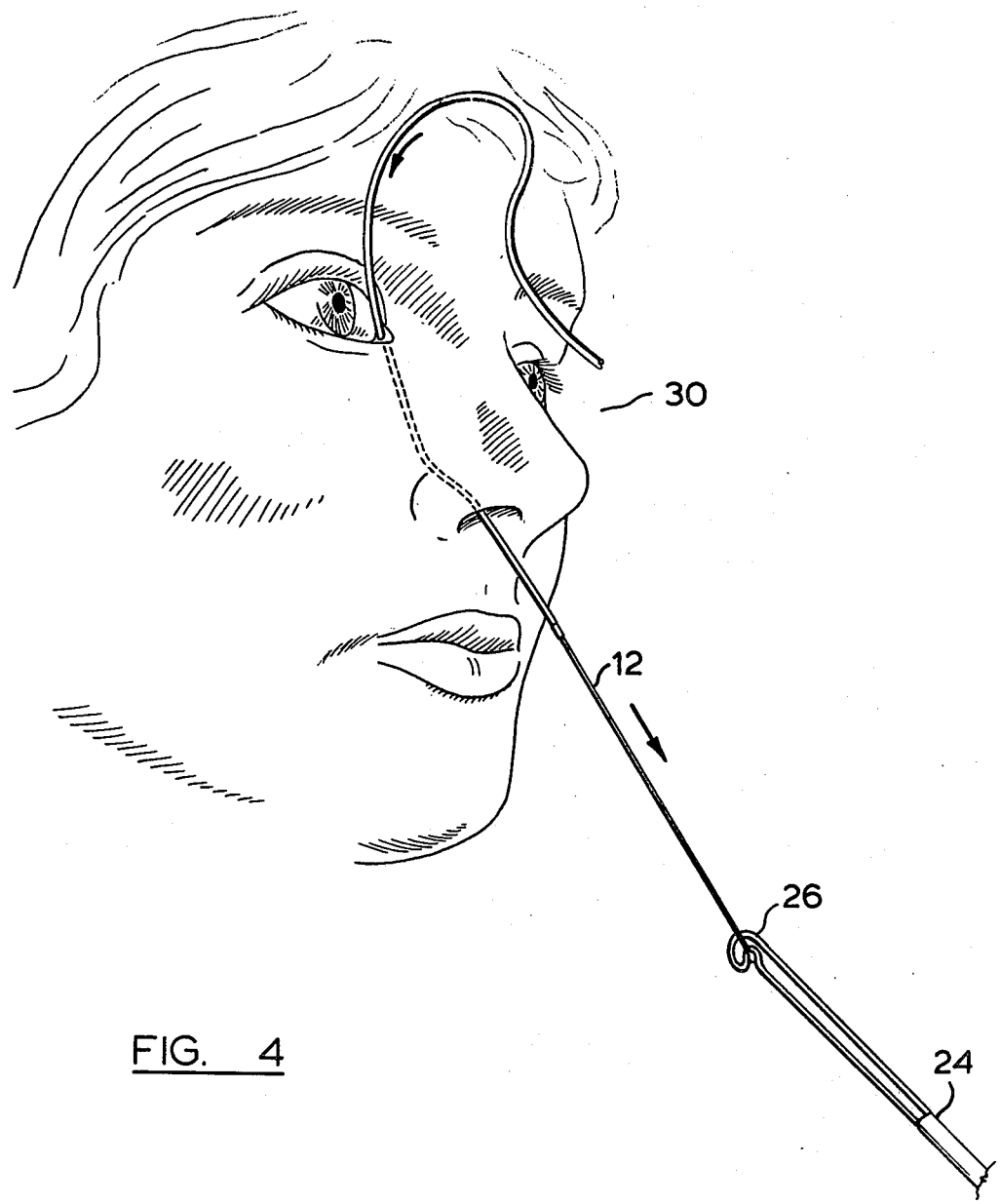

Reference is first made to FIG. 1 which illustrates a canaliculus intubation set indicated generally by the numeral 10 and consisting of a pair of thin probes 12, 14 fitted to respective ends of a tube 16 of silicone rubber which by its nature is quite limp and very flexible.

The probe 12 is typical also of probe 14 and includes an enlarged distal end portion 18 and a tapered enlargement 20 adjacent its proximal end. End portion 18 is rounded and the enlargement 20 has an external size comparable to that of the tube 16.

The preferred probes 12 and 14 are formed from a relatively fine tempered steel wire having a diameter of 0.040 cm and a length of about 12 cm. Such a probe has a small resistance to deflection but is tempered so that it does tend to retain its original shape after being subjected to small deflections. The probe will move through the lacrimal duct when pushed downwards and unlike prior art, will tend to follow the shape of the duct. Such a fine wire would puncture tissue if the end portion 18 were not included. This end portion is preferably made from solder attached to the end of the probe and the enlargement 20 is formed in similar fashion. The end portion 18 should be generally spherical so that there is a limited possibility of damage caused by the end of the probe being forced to penetrate or scratch soft tissue.

The tube 16 is preferably of silicone rubber having a length of about 23 cm, an internal diameter of 0.03 cm, and an external diameter of 0.06 cm. (Preferred tubing is sold by Dow Corning as Silastic Medical Grade Tubing, Catalogue No. 602,101). It will be appreciated from the above dimensions that the tubing 16 is a force fit over the end of the probes and is located by engagement with the tapered enlargement 20. If preferred, the tube can be bonded to the probes using a medical grade adhesive such as that sold by Dow Corning as Type A, Catalogue No. 891.

Before describing the use of the probe set shown in FIG. 1, a tool suitable for use with this set will be described with reference to FIG. 2. As seen in this figure, a tool 21 consists of a handle portion 22 having an aligned extension 24 terminating in a hoop portion 26. The hoop portion is formed from a stiff wire and includes a recess 28 which extends forwardly and inwardly from an opening at the side of the extension. The recess has a width corresponding generally to that of the diameter of the probes 12, 14 for use as will be described.

Reference is next made to FIG. 3 which illustrates the probe set 10 in use. The patient 30 has received probe 12 which has been pushed downwardly through the lacrimal duct and into the inferior meatus. At this point, the end portion 18 of the probe is in engagement with the lower wall of the meatus and the probe must be deflected through approximately 90 degrees to allow the end portion to be withdrawn. As described, the probe is readily deflected so that this deformation can take place without undue force resulting in damage to surrounding tissue. Although a tool such as a Kelly clamp can be used to withdraw the end of the probe 12 from the nasal passage, more conveniently the tool shown in FIG. 2 is used.

As indicated in FIG. 3, the tool 21 is entered into the nasal passage with the extension 24 projecting inwardly. It will be evident that it is a relatively simple matter to engage the probe 12 in the recess 28 (FIG. 2) of the tool and that when the tool is then withdrawn the end portion 18 will be trapped in the recess 28 so that the tool can be used to draw the probe through the nasal passage and outwardly as illustrated in FIG. 4. This draws the tube 16 into the lacrimal duct. The process can be repeated using the probe 14 (FIG. 1) in the opposite canaliculus outflow system and after intubation of both systems the tube is cut leaving a portion in the canaliculus systems. The tube is then left in place for a period determined by the type of damage being corrected or repaired and then subsequently removed.

Although it is possible that the probe set could be made from other than the preferred materials, the probe should be sufficiently flexible to permit it to be bent readily to take the contour necessary to permit the end portion to be withdrawn from the nasal passage and for the rest of the probe to follow the end portion.

Throughout this description an attempt is made to draw a distinction between prior art structures and the present probe. Although it is appreciated that all of the prior art probes have a degree of flexibility, they are designed to be quite stiff because it was previously thought that such stiffness was necessary to permit the probe to be inserted. It has now been found that a thin flexible probe having an enlarged end can be pushed through the lacrimal duct. This probe follows the path of the lacrimal duct and can be very readily deflected to draw it out of the nasal meatus. A stiffer wire such as that taught by Guibor needs larger forces to deflect it and a relatively large reaction force must then be absorbed by tissue associated with the lacrimal duct. Such forces are preferably avoided.

What we claim is:

1. A probe set for use in the canaliculus intubation of the lacrimal duct, the probe set comprising:
    a probe of a light wire which can be readily deflected through an angle of at least 90 degrees to permit the probe to pass from the nasolacrimal duct to the nasal inferior meatus, the probe having an enlarged end portion which is rounded to limit the possibility of damage to tissue when the probe is inserted; and
    a very flexible tube of minimal rigidity having a first end containing an end of the probe remote from the end portion and having an outside diameter comparable to that of the end portion so that in use as the probe is inserted the enlarged end portion minimises damage to tissue and can be used to pull this end from the nasal passage to thereby draw the tube into the lacrimal duct.

2. A probe set as claimed in claim 1 and further comprising a second probe having an end contained in the other end of the tube.

3. A probe set as claimed in claim 1 in which the tube is of silicone rubber.

4. A probe set as claimed in claim 1 in which the probe is of tempered stainless steel wire having a diameter of 0.040 cm.

5. The combination of a probe set as claimed in claim 1 and a tool for pulling the probe from the nasal inferior meatus, the tool having a hook portion defining a recess having a width greater than the thickness of said light wire and smaller than the enlarged end portion so that recess is adapted to receive the probe but to prevent passage of the end portion through the recess as the tool is used to pull the probe from the nasal inferior meatus thereby moving the tube into the lacrimal duct.

6. A probe set as claimed in claim 2 in which the tube is of silicone rubber.

7. A probe set as claimed in claim 2 in which the probe is of tempered stainless steel wire having a diameter of 0.040 cm.

8. A method of canaliculus intubation of the lacrimal duct comprising the steps:

providing a probe of light wire which can be deflected readily as it emerges from the lacrimal duct into the nasal inferior meatus, the probe having an enlarged end portion which is rounded to limit the possibility of damage to tissue when the probe is inserted, and a very flexible tube of minimal rigidity engaged over an end of the probe remote from the enlarged end portion and having an outside diameter comparable to that of enlarged end portion;

inserting the enlarged end portion to the lacrimal duct at the eye and moving this end portion downwardly through the duct into the nasal inferior meatus until the enlarged end portion meets the floor of the nasal cavity;

providing a tool having a hook portion defining a recess proportioned to receive the light wire and to prevent passage of the enlarged end portion through the recess;

engaging the tool in the nasal cavity to contact the light wire and, manipulating the tool so that the light wire is contained in the recess;

gently drawing the tool outwardly bringing with it said end portion so that the light wire curves freely from the lacrimal duct into the inferior meatus out of said nasal passage, said probe being drawn outwardly until the tube is positioned in the lacrimal duct;

severing excess end portions of the tube to leave the required part of the tube in the lacrimal duct.

* * * * *